United States Patent [19]
Murrer et al.

[11] Patent Number: 5,968,976
[45] Date of Patent: Oct. 19, 1999

[54] PHARMACEUTICAL COMPOSITION CONTAINING SELECTED LANTHANUM CARBONATE HYDRATES

[75] Inventors: Barry A Murrer; Nigel A Powell, both of Berkshire, United Kingdom

[73] Assignee: AnorMed Inc., Langley, Canada

[21] Appl. No.: 08/913,960

[22] PCT Filed: Mar. 19, 1996

[86] PCT No.: PCT/GB96/00575

§ 371 Date: Jan. 2, 1998

§ 102(e) Date: Jan. 2, 1998

[87] PCT Pub. No.: WO96/30029

PCT Pub. Date: Oct. 3, 1996

[30] Foreign Application Priority Data

Mar. 25, 1995 [GB] United Kingdom .................. 9506126

[51] Int. Cl.⁶ .................................................. A01N 55/02
[52] U.S. Cl. ..................... 514/492; 514/512; 424/715; 534/16
[58] Field of Search .............. 534/16; 514/492, 514/512; 424/715

[56] References Cited

PUBLICATIONS

Yanagihara et al., "Synthesis of Lanthanide Carbonates", Journal of the Less–Common Metals, 167(2) pp. 223–232, 1991.

Patent Abstract of vol. 11, No. 371, (C–462), Dec. 3, 1987 & JP, A, 62 145024 (Asahi Chem Ind Co Ltd), Jun 29, 1987.

Chemical Abstracts, vol. 107, No. 26, Dec. 28, 1987, abstract No. 249009, Mineely et al., "Molten potassium pyrosulfate: reactions of lanthanum metal and six of its compunds", XP002010788, see abstract, Aust. J. Chem. 40(7), pp. 1309–1314, 1987.

Chemical Abstracts, vol. 104, No. 26, Jun. 30, 1986, abstract No. 236218, Mzareulisvili et al., "Study of interaction of lanthanum nitrate with alkali metal and ammonium carbonates", XP002010789, Soobshch. Akad. Nauk Gruz. 121(1), pp. 81–84, (1986).

Chemical Abstracts, vol. 87, No. 20, Nov. 14, 1977, abstract No. 161013, Oda et al., "Studies on the crystal water of lanthanum carbonates", XP002010790, Oita Daigaku Kyoikygakubu Kenku Kiyo, Shizen Kagaku, 4(5), pp. 1–6, 1975.

*Primary Examiner*—Dwayne C. Jones
*Attorney, Agent, or Firm*—Morrison & Foerster, LLP

[57] ABSTRACT

Selected lanthanum carbonate hydrates may be administered into the gastrointestinal tract, to treat hyperphosphataemia in patients with renal failure.

10 Claims, 4 Drawing Sheets

PHARMACEUTICAL COMPOSITION CONTAINING SELECTED LANTHANUM CARBONATE HYDRATES

This application is a 371 of PCT/GB96/00575 filed on Mar. 19, 1996.

This invention concerns a novel and inventive pharmaceutical composition and method, more particularly it concerns a composition for the treatment of hyperphosphataemia.

Hyperphosphataemia is a particular problem of patients with renal failure, using dialysis equipment. Conventional dialysis fails to reduce levels of phosphate in the blood, so that the levels rise in time. It is known to control phosphate levels by the oral administration of aluminium salts, or calcium salts. With the known toxic effects of aluminium, aluminium-based therapy tends to be avoided. In the case of calcium salts, calcium is absorbed rather readily from the gut, and in turn causes hypercalcaemia.

It has been suggested (Nakagawa et al, Trans Am Soc Intern Organs, 31, (1985) 155–9) that hydrous cerium oxide could be used as a bead in an ion-exchange column, to bind phosphate during dialysis. Japanese published patent application 61 004 529 appears to cover the same idea, suggesting that the hydrous oxides of La, Ce and Y may be used in the column. However, although the rare earths are generally considered of low toxicity according to the Hodge-Sterner classification system (Am Ind Hyg Assoc Quart, 10, (1943), 93), their toxicity when given iv, which corresponds to use in a blood dialysis system, is significant and we are not aware that the suggested ion exchange system or any development thereof has met with widespread acceptance or has been tested clinically for hyperphosphataemia.

It appears that cerium oxide or oxalate was administered many years ago for different medical indications, but that this has fallen into complete disuse.

Japanese published patent application number 62-145024 (Asahi Chemical Ind KK) discloses that rare earth carbonates, bicarbonates or organic acid compounds may be used as phosphate binding agents. One example of said published application relates to the use of lanthanum carbonate, although in the tests described, cerium organic acid salts and carbonate gave better phosphate ion extraction than lanthanum carbonate. Example 11 of said published application prepares $La_2(CO_3)_3.H_2O$, ie the monohydrate; all the other Examples are directed to rare earth carbonates other than lanthanum carbonate.

We have now discovered that certain forms of lanthanum carbonate exhibit improved performance in a variety of tests, over standard commercial lanthanum carbonate, which is believed to be the octahydrate form, and over $La_2(CO_3)_3.H_2O$ or similar compounds.

According to one aspect therefore, the present invention is the use of lanthanum carbonate of formula $La_2(CO_3)_3.xH_2O$ where x has a value from 3 to 6, preferably from 3.5 to 5, more especially from 3.8 to 4.5, for the preparation of a medicament for the treatment of hyperphosphataemia by administration into the gastrointestinal tract.

The invention further provides a pharmaceutical composition comprising said lanthanum carbonate, in admixture or association with a pharmaceutically acceptable diluent or carrier, in a form for administration into the gastrointestinal tract for the treatment of hyperphosphataemia.

The invention may also be expressed as a method of treatment of hyperphosphataemia in a patient with renal failure, comprising the administration of an effective dose of said lanthanum carbonate into the gastrointestinal tract.

According to another aspect, the present invention is a process for the preparation of lanthanum carbonate which comprises the steps of:

(i) reacting lanthanum oxide with an acid which gives a soluble salt of lanthanum;

(ii) reacting a solution of the thus obtained lanthanum salt with an alkali metal carbonate to produce a wet cake of lanthanum carbonate octahydrate; and (iii) controlled drying of the wet cake of lanthanum carbonate octahydrate so as to obtain a lanthanum carbonate with 3 to 6 molecules of water of crystallisation.

According to yet another aspect, the present invention is lanthanum carbonate when obtained by the above-mentioned process.

According to a further aspect, the present invention is lanthanum carbonate of the formula $La_2(CO_3)_3.xH_2O$ where x has a value from 3 to 6.

BRIEF DESCRIPTION OF THE DRAWINGS

Embodiments of the present invention are described below, by way of example only, with reference to the accompanying drawings in which.

Figure 1:
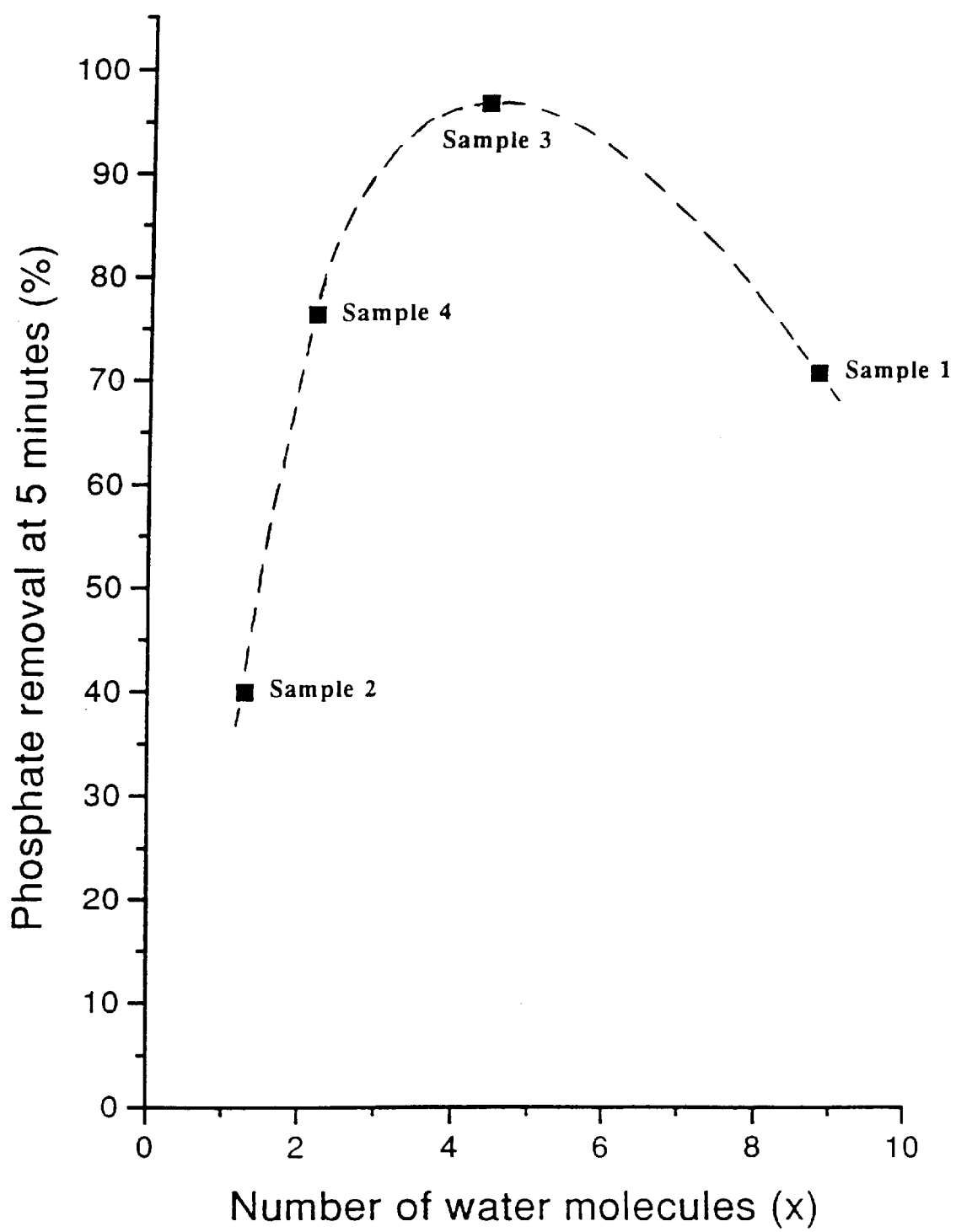
FIG. 1 illustrates the phosphate-binding capability of lanthanum carbonates having different degrees of water of crystallisation.

For the tests described hereinafter, samples of lanthanum carbonate were obtained as follows:

Sample 1. Commercial lanthanum carbonate obtained from a chemical company.

This was characterised by elemental analysis (La, C, H), TGA, X-ray powder diffraction and ir spectroscopy, to have the formula $La_2(CO_3)_3.8.8H_2O$.

Samples 2–4 were prepared by heating portions of Sample 1 at varying temperatures for varying lengths of time, either under vacuum or at atmospheric pressure to obtain materials of formula $La_2(CO_3)_3.xH_2O$ where $0<x<8$.

| Sample | Initial wt (g) | Temp (° C.) | Time (min) | Vacuum (Y/N) | Wt loss (g) | x |
|--------|---------------|-------------|------------|--------------|-------------|-----|
| 2 | 5.00 | 175 | 240 | Y | 1.09 | 1.3 |
| 3 | 20.0 | 80 | 180 | N | 2.6 | 4.4 |
| 4 | 5.01 | 100 | 720* | N | 0.96 | 2.2 |

*Dried to constant weight.

Sample 5 is a sample of lanthanum carbonate which when analysed indicated a formula of $La(CO_3)_3.4H_2O$.

Sample 6 is a sample of lanthanum carbonate prepared according to Example 1 below and having the formula $La_2(CO_3)_3.3.8H_2O$.

In order to show that certain lanthanum carbonate hydrates are significantly different in phosphate binding activity from both lanthanum carbonate octahydrate and from $La_2(CO_3)_3.H_2O$, samples were tested as follows:

i) a stock solution was prepared by dissolving 13.75 g of anhydrous $Na_2HPO_4$, 8.5 g of NaCl in 1 litre deionised water.

ii) 100 ml of the stock solution was adjusted to pH3 by the addition of concentrated HCl.

iii) A 5 ml sample was taken and filtered through a 0.02 μm filter to give a Time 0 sample. This was analysed for phosphate using a Sigma Diagnostics Colorimetric Phosphorus test kit.

iv) 5 ml fresh stock solution was added to reestablish 100 ml, and the pH was re-adjusted to approximately 3.

v) $La_2(CO_3)3.xH_2O$ as a dry powder was added in an amount according to the molecular weight of the particular hydrate, to give a two-fold molar excess of lanthanum over phosphate and stirred at room temperature.

vi) Sampling was carried out at time intervals from 0.5 to 10 minutes, and the percentage of phosphate was determined as in iii) above. The results are shown in the Table 1 below.

TABLE 1

| TIME | % PHOSPHATE REMOVED Sample | | | | | |
|---|---|---|---|---|---|---|
| (Minutes) | 1 | 2 | 3 | 4 | 5 | 6 |
| 0 | | | | | | |
| 0.5 | | 13.4 | 18.8 | 15.1 | 22.9 | 31.4 |
| 1 | 29 | 18.4 | 31.5 | 26.8 | 40.4 | 55.5 |
| 1.5 | | 25.4 | 43.1 | 36 | 55.2 | 74.8 |
| 2 | | 28.1 | 50.6 | 45.3 | 69.5 | 88.1 |
| 2.5 | | 30.8 | 60.5 | 51.8 | 79.9 | 95.3 |
| 3 | | 34.4 | 69 | 57.6 | 90.3 | 99.6 |
| 4 | | | | | | 100 |
| 5 | 70.5 | 39.9 | 96.5 | 76.3 | 100 | 100 |
| 10 | 100 | ND | 99.1 | ND | 100 | 100 |

It can readily be seen from Table 1 that Sample 3 ($La_2(CO_3)_3.4.4H_2O$); Sample 5 ($La_2(CO_3)_3.4H_2O$) and Sample 6 ($La_2(CO_3)_3.3.8H_2O$ appreciably quicker than the $8.8H_2O$, $.1.3H_2O$ or $2.2H_2O$ forms. We believe that the results for $La_2(CO_3)_3.1.3H_2O$ are in agreement with the results shown in the above mentioned Japanese published patent application number 62-145024 where for $La_2(CO_3)_3.H_2O$, only 90% removal is shown after 120 minutes.

It can also be readily seen from FIG. 1 of the accompanying drawings that the highest phosphate removal is obtained with lanthanum carbonates having 3 to 6 molecules of water.

The present invention offers the possibility of binding phosphate without any incursion of lanthanum into the blood stream, where toxic effects can cause problems. The specified lanthanum carbonate has negligible absorption from the gut, as shown by the in vivo tests described below.

Throughout this document, the term "treatment" is intended to include preventative treatment.

Processes for preparing lanthanum carbonates according to the present invention are described by way of illustration in the following Examples 1 and 2.

EXAMPLE 1

Lanthanum oxide (1.5 kg, 4.58 mol) was suspended in water (5.5 litres) in a 20 litre flask. Nitric acid (Analar grade, 69%, SG 1.42, 1.88 litres, 29.23 mol) was added to the stirred solution over 1.5 hours at such a rate as to keep the temperature between 60–80° C. The resulting lanthanum nitrate solution was left to cool to room temperature and filtered. A solution of sodium carbonate (1.65 kg, 15.57 mol) in water (7.75 litres) was added to the stirred lanthanum nitrate solution over 45 minutes. At the end of the addition the pH of the suspension was 9.74. The suspension was left overnight, filtered (Buchner funnel, 540 paper) and dried on the filter in a current of air for 30 minutes. The solid was then re-suspended in water, stirred for 40 minutes and filtered. This procedure was repeated to give a total of six washes, when the nitrate concentration in the filtrate was <500 ppm. The final material (4.604 kg) was divided between three Pyrex dishes and a sample from each analysed for water content. (By decomposition of weighed sample of $(La_2(CO_3)_3.xH_2O$ at 1050° C., 2 hours to $La_2O_3$). The dishes were then placed in a fan oven at 80° C. and the weight loss of each dish monitored until the material of the required degree hydration was obtained. The progress of the drying is shown below

| Time | mol H$_2$O/La | | |
|---|---|---|---|
| (hours) | Dish 1 | Dish 2 | Dish 3 |
| 3.50 | 10.9 | 13.5 | 12.6 |
| 12 | 5.7 | 6.0 | 5.2 |
| 14 | 5.3 | 5.4 | 4.6 |
| 16 | 4.9 | 5.1 | 4.3 |
| 17 | 4.4 | 4.6 | 3.8 |
| 19.5 | 3.8 | 4.0 | 3.2 |

Figure 2:
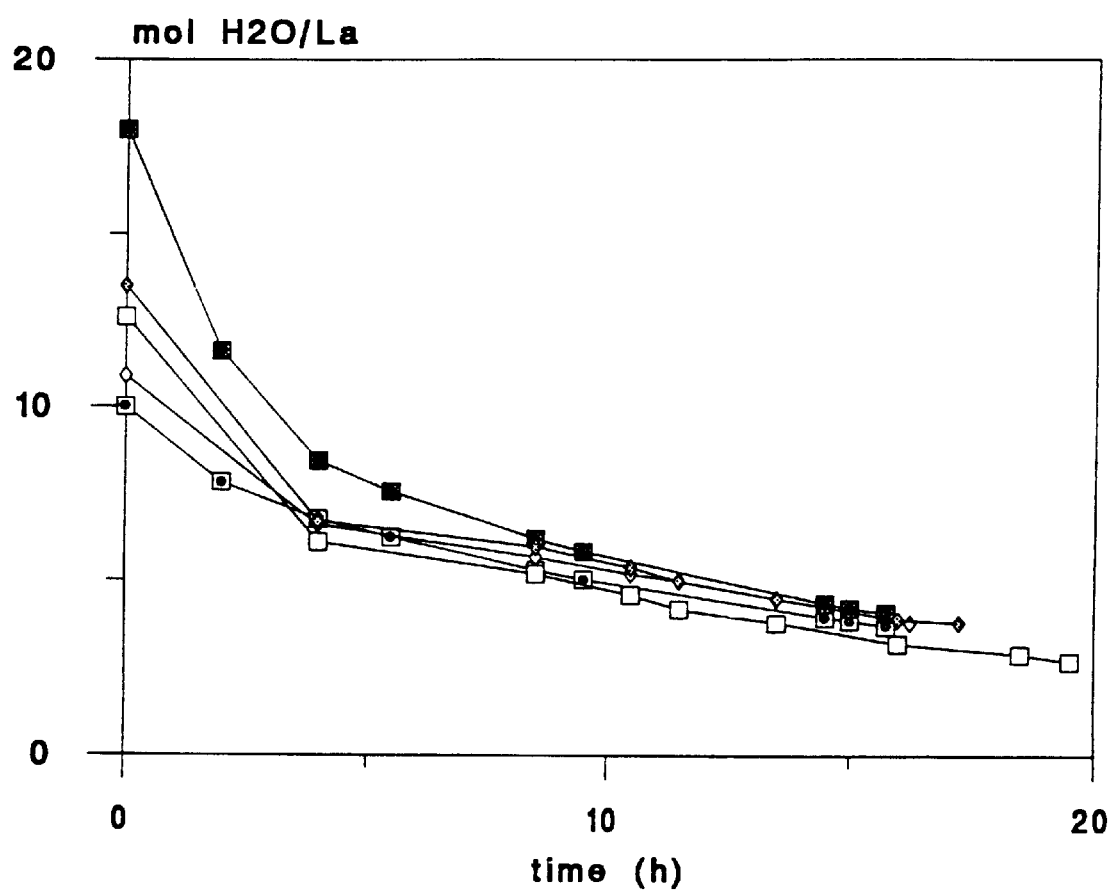
FIG. 2 illustrates the drying curves for five batches of lanthanum carbonate prepared by the method indicated in Example 1.

Drying curves for five batches produced by this route are shown in FIG. 2.

$La_2(CO_3)_3.3.8H_2O$ from dish 1 was selected as Sample 6 for the phosphate binding tests set forth in Table 1.

EXAMPLE 2

The process of Example 1 was repeated but using hydrochloric acid (12.28M, 2.48 litres) in place of nitric acid to dissolve lanthanum oxide (1.5 kg). The yield of crude product after six washes was 4.378 kg. The product was divided in three approximately equal portions in Pyrex dishes and dried in a fan oven at 80° C. After 2 hours a sample was taken from each tray and water analysed by decomposition to lanthanum oxide as described above. These figures were used to calculate the weight loss needed to give material of the required composition. The time course of the drying process is shown below.

| Time | mol H$_2$O/La | | |
|---|---|---|---|
| (hours) | Dish 1 | Dish 2 | Dish 3 |
| 2 | 21.3 | 22.1 | 20.4 |
| 5.5 | 12.3 | 13.2 | 12.2 |
| 9 | 7.9 | 8.0 | 7.6 |
| 11.5 | 6.9 | 7.0 | 6.6 |
| 17 | 4.9 | 5.1 | 4.6 |
| 18.5 | 4.6 | 4.8 | 4.2 |
| 19.5 | 4.4 | 4.6 | 4.1 |
| 20 | 4.3 | 4.6 | 4.0 |

Samples were taken from each dish, combined and analysed. The following results were obtained:

| | Found | Calculation for $La_2(CO_3)_3.4H_2O$ |
|---|---|---|
| % La (gravimetric) | 52.38% | 52.4% |
| carbonate (titration) | 5.76 mol/g | 5.66 mol/g |
| H$_2$O (NMR) | 13.06% | 13.59% |

Figure 3:
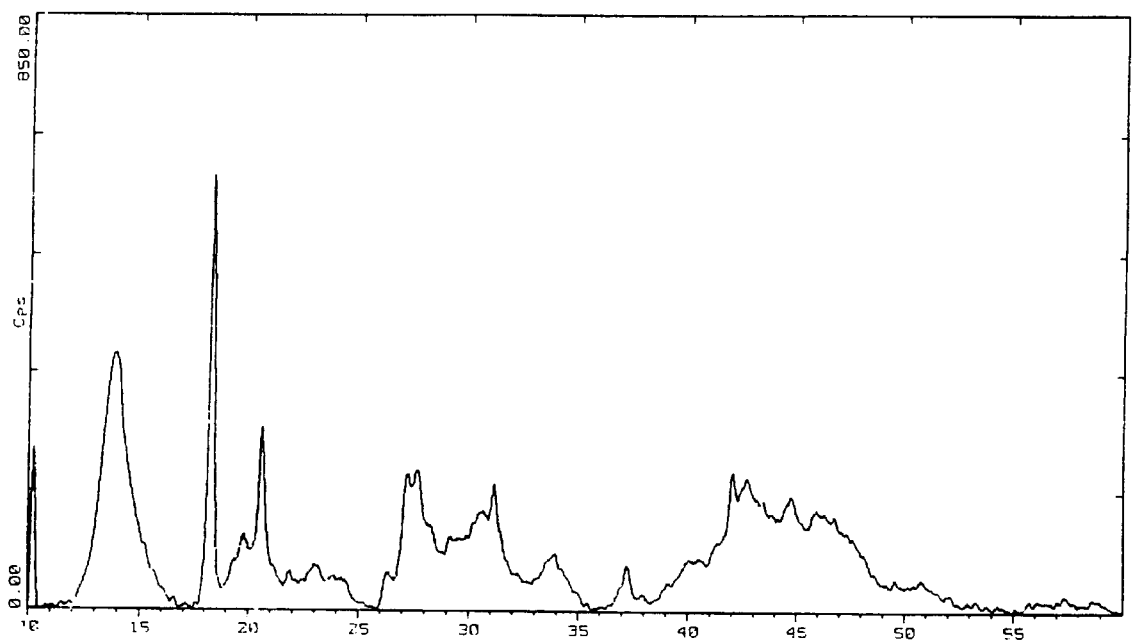
FIG. 3 illustrates the XRD analysis of lanthanum carbonate $4H_2O$ prepared by the method indicated in Example 2.

The XRD analysis for lanthanum carbonate $4H_2O$ prepared by the method of Example 2 is illustrated in FIG. 3.

Figure 4:
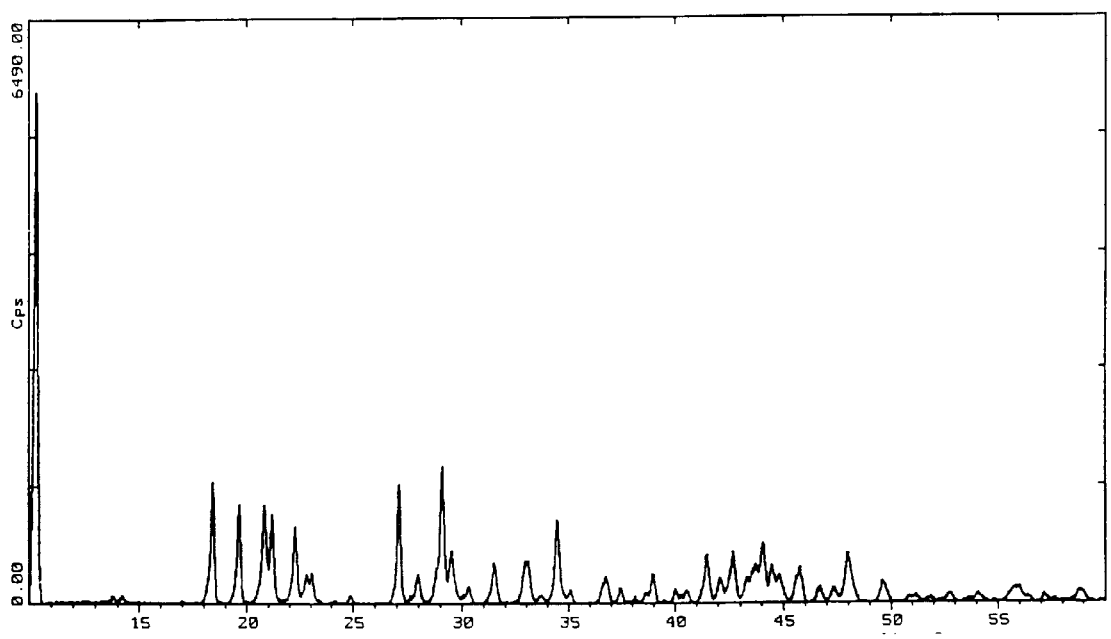
FIG. 4 illustrates the XRD analysis of lanthanum carbonate $8.8H_2O$ of Sample 1 above.

FIG. 4 illustrates the XRD of lanthanum carbonate 8.8H$_2$O and it is evident that it has a different crystalline structure from lanthanum carbonate 4H$_2$O prepared by the method of Example 2. The XRD analysis of lanthanum carbonate 4H$_2$O prepared by the method of Example 1 was similar to the XRD analysis of lanthanum carbonate 4H$_2$O prepared by the method of Example 2.

Pharmaceutical compositions for oral administration according to the invention may be formulated and manufactured using methods well known in the art. Suitable diluents or carriers are also well known. The compositions may desirably be in a dosage form, to provide a single daily dose, or a number of sub-daily dosages. Conventional pharmacological methods may be used to ascertain suitable dose levels. The level of phosphate in the food that an individual ingests is important. Daily dosages are indicated to be in the range 0.1 to 50 g, preferably about 0.5 to 15 g. Suitable forms for oral administration include solid forms such as tablets, capsules and dragees and liquid forms such as suspensions or syrups. In addition to diluents and carriers, it is conventional in the formulation of oral preparations to include non-active ingredients such as thickeners, taste-improving components and colouring agents. The said carbonate may also be coated or treated to provide delayed-release forms. Preferably, the required daily dosage is given in tablet form, eg chewable tablet form, to be taken with meals. A suitable daily dosage of about 2 g for 70 kg man, should be compared with a daily dosage of 20 g for a commercial calcium-based phosphate binding composition.

To demonstrate that the lanthanum carbonate of the invention (or lanthanum phosphate formed after binding to phosphate in the gut) is fully excreted and does not pass out of the gut into the circulation system when given orally, three rats were dosed with 20 mg/kg of La$_2$(CO$_3$)$_3$.4H$_2$O (Sample 5) and kept in metabolic cages where faeces and urine could be collected. The results are shown in Table 2 below.

| Animal No. | Time (hours) | % La Recovered |
|---|---|---|
| 1 | 24 | 103.2 |
| 1 | 48 | 0.1 |
| 1 | 72 | <0.2 |
| 1 | Total | 103.3 |
| 2 | 24 | 75.3 |
| 2 | 48 | 23 |
| 2 | 72 | 1.2 |
| 2 | Total | 99.5 |
| 3 | 24 | 93.8 |
| 3 | 48 | 10 |
| 3 | 72 | 0.1 |
| 3 | Total | 103.8 |

It can be seen that after 72 hours, all of the lanthanum has been excreted. In the urine samples, the amount of lanthanum was below detection limits. After the test, the rats were sacrificed, and kidney, liver and femur were analysed for lanthanum. In all cases, the amount of lanthanum was below 0.1 ppm.

We claim:

1. A pharmaceutical composition for the treatment of hyperphosphataemia comprising lanthanum carbonate of the formula

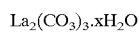

where x has a value from 3 to 6, in admixture with a pharmaceutically acceptable diluent or carrier in a form for administration to the gastrointestinal tract.

2. A composition according to claim 1, wherein x has a value from 3.5 to 5.

3. A composition according to claim 2, wherein x has a value from 3.8 to 4.5.

4. A composition according to any one of claims 1 to 3 in unit dosage form to provide from 0.1 to 20 g/day.

5. A process for the preparation of lanthanum carbonate as defined in any one of claims 1 to 3 which comprises the steps of:
 (i) reacting lanthanum oxide with hydrochloric acid to obtain lanthanum chloride;
 (ii) reacting a solution of the thus obtained lanthanum chloride with an alkali metal carbonate to produce a wet cake of lanthanum carbonate octahydrate; and
 (iii) drying the wet cake of lanthanum carbonate octahydrate so as to obtain a lanthanum carbonate with 3 to 6 molecules of water of crystallisation.

6. A process as claimed in claim 5 wherein the alkali metal carbonate is sodium carbonate.

7. A method to treat hyperphosphataemia in a subject which method comprises administering to said subject an amount of lanthanum carbonate of the formula

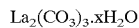

wherein x has a value from 3 to 6 effective to treat said hyperphosphataemia.

8. The method of claim 7 wherein x has a value from 3.5 to 5.

9. The method of claim 8 wherein x has a value from 3.8 to 4.5.

10. The method of any of claims 7–9 wherein said administering is by an oral route.

* * * * *